(12) United States Patent
Gijsbers et al.

(10) Patent No.: US 6,447,500 B1
(45) Date of Patent: Sep. 10, 2002

(54) BRAIN FLUID ION CONCENTRATION MODIFICATION FOR TREATING NEUROLOGICAL DISORDERS

(75) Inventors: Johan F. M. Gijsbers, Munstergeleen; Frans L. H. Gielen, Eckelrade, both of (NL)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/561,550

(22) Filed: Apr. 28, 2000

(51) Int. Cl.[7] .......................... A61M 31/00; A61B 19/00
(52) U.S. Cl. ........................... 604/500; 128/898
(58) Field of Search .................... 604/4.01, 27, 28, 604/29, 500, 503, 504, 65, 66, 131; 128/897, 898

(56) References Cited

U.S. PATENT DOCUMENTS

| | | | |
|---|---|---|---|
| 5,832,932 A | * 11/1998 | Elsberry et al. | ............ 128/898 |
| 5,978,702 A | * 11/1999 | Ward et al. | ............... 607/3 |
| 6,018,682 A | * 1/2000 | Rise | ............... 607/45 |
| 6,263,237 B1 | * 7/2001 | Rise | ............... 607/3 |
| 6,272,370 B1 | * 8/2001 | Gillies et al. | ............... 600/411 |

* cited by examiner

Primary Examiner—Sharon Kennedy
(74) Attorney, Agent, or Firm—Banner & Witcoff, Ltd.

(57) ABSTRACT

Epilepsy and other neurological disorders that are affected by the electrical potential difference between intracellular fluid and extra-cellular fluid and therefore the cell membrane potentials, and therefore the thresholds for the communication between brain cells can be controlled by re-circulating extra-cellular brain fluid after the fluid has been treated to alter its ion concentrations. A computer-controlled pump can precisely control the extraction and delivery of brain fluid after the ion concentration of the fluid is appropriately adjusted, e.g. guided by the Goldmann equation. Well-known techniques for modifying ion concentrations can be used to raise or lower ion concentrations as needed.

20 Claims, 2 Drawing Sheets

BRAIN FLUID ION CONCENTRATION MODIFICATION FOR TREATING NEUROLOGICAL DISORDERS

FIELD OF THE INVENTION

This invention relates to methods of treating medical disorders. In particular, this invention relates to a method of treating the cause of epilepsy, which is rooted in the basic concepts described by the Goldman equation. This equation describes the relation between the cell rest membrane potential and the concentration of ions inside and outside the cells in e.g. nervous and muscle tissue. This implies that cell excitability can be modified and therefore the physiological inter-connectivity between cells. This interconnectivity is a major factor in the generation of e.g. epilepsy. The key concept of this invention is that if cell rest membrane electrical potentials are modified, epilepsy, and perhaps other neurological disorders might be effectively controlled.

BACKGROUND OF THE INVENTION

Epilepsy is a debilitating neurological disorder. Functional control of many or all body functions can be lost and further permanent brain damage results from each generalized epileptic attack.

It is known that an epileptic seizure is manifested by an uncontrolled propagation of nerve impulses throughout the nerve cells in certain, areas of the brain. The nerve impulses of an epileptic seizure are characterized by many synchronized discharges, which may involve the whole brain. As a consequence the control of many body functions is lost. During epileptic seizures, the normal physiological inter-connectivity between brain cells is greatly altered, resulting in a synchronized highly pathological brain activity.

It is well known that the normal, electrical, rest membrane potential difference between intra-cellular fluid (fluid enclosed by the cell membrane) of brain cells and the extra-cellular brain fluid (fluid outside the membrane) is about −0.07 volts (−70 millivolts or mV.) The intra-cellular brain fluid is at a more negative potential than the extra-cellular fluid potential. If this potential becomes more negative (cells are hyper-polarized), the likelihood of an epileptic seizure is decreased. In the field of biophysics, the well known Goldmann equation describes how the membrane potential depends on the concentrations of ions in the intra- or extra-cellular medium. Consequently this equation describes how changes in the extra-cellular ion concentrations will result in a hyper-polarization of brain cells which will result in suppression of epileptic seizures.

SUMMARY OF THE INVENTION

A method of treating epilepsy whereby seizures can be suppressed or prevented by using extra-cellular fluid (in the central nervous system, cerebral spinal fluid or "CSF") that is extracted from the brain, e.g. from one of the brain ventricles. The extracted brain fluid is treated to change the concentration of ions in the fluid in such a way that cells surrounded by this modified fluid will be hyper-or hypo-polarized which is quantitatively predicted by the Goldmann equation. The ion-adjusted fluid is re-injected into the brain into a specific brain structure, which may contain the brain cells that generate the epileptic seizure (hyper-polarization needed) or in a brain structure that modulates the epileptic region (hyper-polarization needed for suppressing structures and hypo-polarization needed for activating structures). The increased negative potential difference (hyper-polarization) between the intra and extra-cellular fluid in the epilepsy-generating brain structure increases the potential difference that the nerve cells must overcome to be involved in the generation of an epileptic seizure. In effect, the invention includes modulating the interconnectivity of nerve cells by modulating the rest membrane electrical potential.

DETAILED DESCRIPTION OF THE PREFERRED EMBODIMENT

Figure 1:
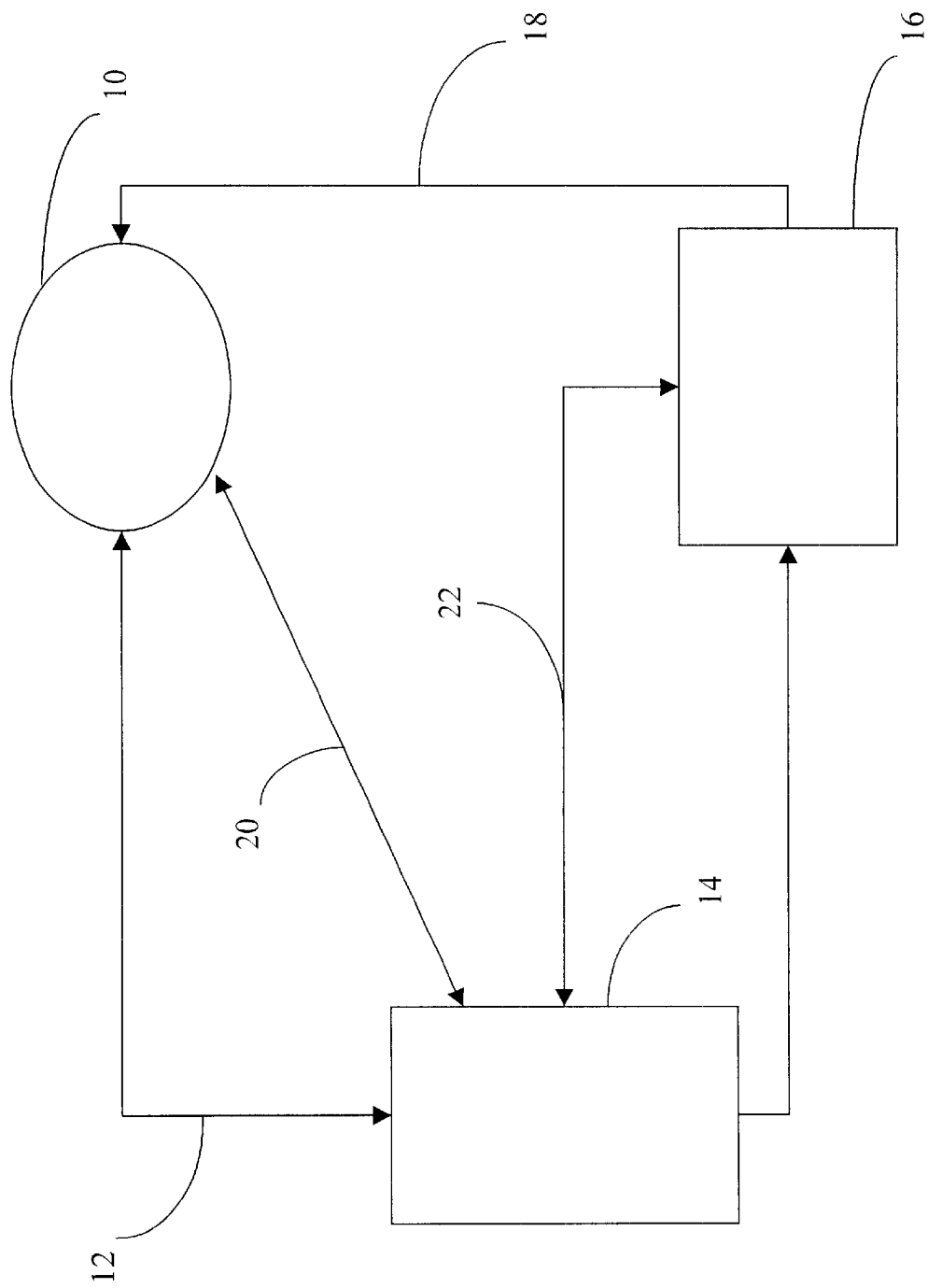
FIG. 1 shows the steps of the method contemplated herein.

FIG. 1 shows a simplified schematic block diagram for a mechanical system for treating epilepsy and other neurological disorders by modifying ion concentration in brain fluid. In FIG. 1, fluid from a patient's brain 10 (the fluid is not shown) is extracted from the brain (preferably from 1 of the brain ventricles) 10, by a pump 14. Extra-cellular fluid can be extracted by exerting a relatively negative pressure on a small-diameter flexible conduit (i.e. a catheter or capillary tube 12) one end of which is coupled to the pump and which provides the negative pressure. The other end of the flexible conduit is inserted into the brain ventricle. Extra-cellular brain fluid is drawn through an appropriately-sized capillary tube or catheter 12 to the pump 14, which in the preferred embodiment was a positive displacement computer-controlled pump 14.

In the preferred embodiment, the pump 14 (which may be computer controlled) reads and executes stored program instructions that cause the pump to pump the extracted fluid according to the program and its parameters. In many applications, ion-adjusted fluid will be pumped in an "open loop" fashion, i.e. according to some predetermined schedule in the pump's stored program. Open-loop delivery methods can be based upon either the volume of modified extra-cellular brain fluid to be delivered per unit time or some other parameter.

The pump 14 forces extracted extra-cellular brain fluid through an ion concentration adjustment mechanism 16. Ion concentrations in the extracted brain fluid are modified in the ion concentration adjustment mechanism 16. The ion concentration of the fluid can be adjusted by methodologies well known in the art including, but not limited to, appropriate ion exchange mechanisms; filtration, or chemical treatment. The ion concentration adjustment mechanism 16 changes the ion concentration in brain fluid such that when the fluid is returned to the brain, the brain fluid ion concentration, at least in localized regions, is modified. Output from the ion concentration adjustment mechanism 16 is returned to the brain 10 through an appropriately sized capillary tube or catheter 18.

Figure 2:
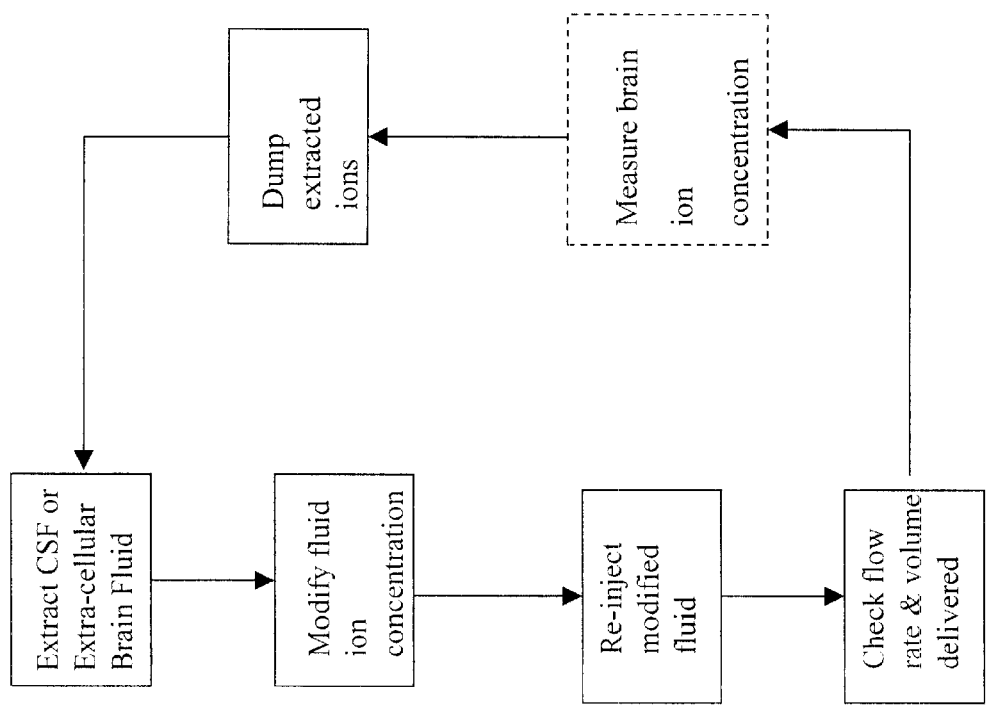
FIG. 2 shows a simplified block diagram of an apparatus that could perform the method disclosed and claimed herein.

Procedural steps of the method 200 of the invention are illustrated in FIG. 2. CSF or extra-cellular brain fluid is extracted 210 and the ion-concentration of the fluid is adjusted 220 using an appropriate methodology. Some techniques for modifying ion concentration would include filtering or various chemical treatment processes. After the ion concentration is adjusted, the modified ion-content fluid is re-injected into the patient's brain 230.

At some point in the process, the flow rate of brain fluid from and/or into the patient's brain is measured 240. While this step is shown in FIG. 2 as being after re-injection of the brain fluid 230, alternate methodologies would certainly include deleting this step in its entirety and simply letting the pump run "open loop" doing whatever the program instructions dictate. Still other embodiments would include calculating or measuring the extracted fluid 210 volume as well as the delivered fluid volume. Inasmuch as brain fluid is incompressible, both the extracted and re-injected or delivered fluid volumes should be equivalent, except for any fluid lost during the ion-concentration adjustment.

Still other embodiments might measure the ion concentration in the brain fluid and, depending upon the measured ion concentration, adjust the fluid delivery rate or the ion-concentration adjustment, or both. In an optimum system, a closed-loop feedback system would include a system that measures ion concentration (or other electrical characteristic) and uses this information to control fluid extraction, delivery or ion content so as to achieve the optimum electrical potential difference between the inside and outside of brain cells, imbalances of which might cause epilepsy or other neurological disorders.

Various embodiments of the invention include localized delivery of ion-modulated brain fluid as well as dispersed delivery mechanism, such as a leaky catheter. By replacing the brain fluid at a modified ion concentration, it is possible to change the electrical potential difference between intracellular and extra-cellular brain fluid.

In the preferred embodiment, changing the electrical potential difference across the nerve cell membrane in the epilepsy generating brain structure can significantly affect the occurrence of epileptic seizures. Once a diagnosis of epilepsy is first made or the disease is established, changing the ion concentration in the extra-cellular fluid to increase the potential difference from −70 millivolts to −80 or more millivolts will locally hyper-polarize the brain cells and therefore, can substantially inhibit seizures.

In one of the alternate embodiments, an electrical probe 20 inserted into a localized region of the brain 10 might be read by the computer that controls the pump 14 so as to provide closed-loop feedback so as to even more closely control ion concentrations and therefore more closely control epileptic seizures. A probe inserted into the brain fluid in the brain might measure the ion concentration by the conductivity or resistance of the fluid. In such an embodiment, it is preferable to measure ion concentration after the ion-adjusted fluid has been returned to the patient's brain. The modified resulting membrane potential can be calculated using the well-known Goldman equation. In another alternate embodiment, ion concentrations of extra-cellular fluid might be adjusted according to measured electrical activity of nerve cells in specific brain structures involved in the generation of the epileptic seizures. In such an embodiment, the electrical activity of brain cells, can be continuously adjusted by injecting more or less modified brain fluid in such a way to avoid seizures. Such a closed-loop system could be used to carefully control, in real time, the rate at which ion adjusted fluid is delivered to the brain or to change the ion concentration changes effected by the ion concentration adjustment mechanism 16. A control signal 22 from the computer-controlled pump 14 might be used to change the ion concentration in fluid that is output to the brain 10. In yet another embodiment, it might be possible to alter electrical potential differences across cell membranes simply by adding or administering a predetermined liquid or other substance to brain fluid so as to change the electrical potential across brain cells.

Those skilled in the art will recognize that changing the ion concentration of extra-cellular brain fluid could have other beneficial effects in the treatment of other neurological disorders by adjusting the degree of communication between brain cells. This degree of communication depends on the level of the membrane potential. Hyper-polarized or inhibited cells increase the threshold for cell communication, while hypo-polarized or excited cells decrease the threshold for cell communication. In instances where neurological disorders can be controlled by modulating the communication between brain cells the invention would find the applicability in treating these other disorders.

What is claimed is:

1. A method for treating epilepsy and other neurological disorders of the brain comprising the steps of:
   a) extracting fluid from a brain cavity of a patient;
   b) modifying ion concentrations of said fluid to render modulated ion-content fluid;
   c) returning the modulated ion-content fluid locally into the patient's brain.

2. The method of claim 1 wherein said step c) of returning modulated ion-content fluid into the patient's brain is further comprised of the step c) of: returning modulated ion-content fluid into the patient's brain into at least one localized region of the patient's brain.

3. The method of claim 1 wherein said step c) of returning modulated ion-content fluid into the patient's brain is further comprised of the step of c) pumping said modulated ion-content fluid into the patient's brain according to a predetermined schedule of flow rate.

4. The method of claim 1 wherein said method is further comprised of c): returning modulated ion-content fluid into the patient's brain into a general region of the patient's brain.

5. The method of claim 1 further comprised of the steps of:
   d) measuring ion concentration in said brain fluid after said modulated ion-content fluid, is returned to said patient's brain;
   e) adjusting the delivery of said modulated ion-content fluid, based upon the measured ion concentration of step d).

6. The method of claim 1 further comprised of the steps of:
   d) calculating ion concentration in said brain fluid, using the Goldman equation;
   e) adjusting the delivery of said modulated ion-content fluid, based upon the calculated ion concentration of step d).

7. The method of claim 1 further comprised of the steps of:
   d) measuring the electrical conductivity of said brain fluid after said modulated ion-content fluid, is returned to said patient's brain;
   e) adjusting the delivery of said modulated ion-content fluid, based upon the measured electrical conductivity of said brain fluid.

8. The method of claim 1 wherein delivery of said modulated ion-content fluid is calculated using the Goldman equation.

9. The method of claim 1 wherein the modulated ion-content fluid returned to the brain produces a voltage differential between intra-cellular fluid and extra-cellular fluid, which may be modified to such a level that epileptic seizures are controlled.

10. The method of claim 6 wherein said modulated ion-content fluid is delivered to the patient's brain using closed-loop feedback.

11. The method of claim 1 further comprised of the step of adjusting the delivery of modulated ion-content fluid based upon the measured electrical activity of predetermined most likely epileptic brain cells.

12. The method of claim 2 wherein said modulated ion-content fluid is returned to the brain using a dispersed delivery system.

13. The method of claim 2 wherein said modulated ion-content fluid is returned to the brain ventricle.

14. The method of claim 1 wherein said modulated ion-content fluid is returned to the brain using a computer-controlled pump.

15. The method of claim 1 wherein said modulated ion-content fluid is returned to the brain at a predetermined location by direct injection into a localized region.

16. A method for treating epilepsy and other neurological disorders of the brain comprising the steps of:
   a) diagnosing an epileptic condition in a patient;
   b) substantially continuously extracting fluid from the brain of the patient;
   c) modifying ion concentrations of said fluid to render modulated ion-content fluid using a predetermined process;
   d) substantially continuously pumping the modulated ion-content fluid back into a localized region of the patient's brain;
   e) monitoring the ion concentration of brain fluid proximate to the region where said modulated ion-content fluid is returned to the patient's brain.

17. A system for controlling epileptic seizures comprising:
   a) means for diagnosing an epileptic condition;
   b) a brain fluid pumping mechanism, having an input, coupled to a patient's brain for extracting brain fluid, and having an output;
   c) a fluid ion adjustment mechanism coupled to said output of said brain fluid pumping mechanism, said fluid ion adjustment mechanism having an output from which ion-adjusted fluid is produced;
   d) a catheter, having an input coupled to the output of said ion adjustment mechanism and having an output inserted into a predetermined region of a patient's brain;
   whereby brain fluid is extracted from a patients brain, ion-concentration of said fluid are adjusted and said brain fluid is re-injected into said brain.

18. A system as in claim 17 in which the system includes computer control which reads and executes stored program instructions that cause the pumping mechanism to pump the extracted fluid according to the program and its parameters.

19. A system as in claim 17 or 18 further comprising a probe in the brain providing an output related to measurement of an ion-concentration related brain parameter, the system including computer control which reads the output of the probe to responsively control at least one of fluid extraction, fluid delivery, and ion concentration.

20. A system as in claim 19 in which the computer control calculates ion concentration in brain fluid using the Goldman equation, and adjusts the delivery of modulated ion-content fluid based on the calculated ion concentration.

* * * * *

UNITED STATES PATENT AND TRADEMARK OFFICE
CERTIFICATE OF CORRECTION

PATENT NO. : 6,447,500 B1
DATED : September 10, 2002
INVENTOR(S) : Johan F.M. Gijsbers and Frans L.H. Gielen It is certified that error appears in the above-identified patent and that said Letters Patent is hereby corrected as shown below:

Column 2,
Lines 9-13, reads
"FIG. 1 shows the steps of the method contemplated herein.
FIG. 2 shows a simplified block diagram of an apparatus that could perform the method disclosed and claimed herein." should read
-- FIG. 1 shows a simplified block diagram of an apparatus that could perform the method disclosed and claimed herein.
FIG. 2 shows the steps of the method contempled herein. --

Column 2,
Line 57, reads "...steps of the method 200..." should read -- ...steps of the method... --
Line 59, reads "...extracted 210 and the..." should read -- ...extracted and the... --
Line 60, reads "adjusted 220 using an..." should read -- adjusted using an... --
Line 64, reads "...the patient's brain 230." should read -- ...the patient's brain. --
Line 66, reads "...patient's brain is measured 240." should read -- ...patient's brain is measured. --

Column 3,
Line 1, "brain fluid 230, ..." should read -- brain fluid, ... --
Line 5, reads "...measuring the extracted fluid 210..." should read -- ...measuring the extracted fluid... --

Signed and Sealed this

Twenty-sixth Day of April, 2005

JON W. DUDAS
*Director of the United States Patent and Trademark Office*